US009743917B2

United States Patent
Daly et al.

(10) Patent No.: US 9,743,917 B2
(45) Date of Patent: Aug. 29, 2017

(54) DEVICES FOR APPLYING SURGICAL SEALANTS

(71) Applicant: Cohera Medical, Inc., Pittsburgh, PA (US)

(72) Inventors: Patrick Daly, Pittsburgh, PA (US); Despina Dobbins, Gibsonia, PA (US); Scott Scheeser, Pittsburgh, PA (US)

(73) Assignee: Cohera Medical, Inc., Raleigh, NC (US)

( * ) Notice: Subject to any disclaimer, the term of this patent is extended or adjusted under 35 U.S.C. 154(b) by 0 days.

(21) Appl. No.: 14/577,216

(22) Filed: Dec. 19, 2014

(65) Prior Publication Data

US 2016/0174957 A1 Jun. 23, 2016

(51) Int. Cl.
*A61B 17/08* (2006.01)
*A61B 17/00* (2006.01)
*A61M 39/10* (2006.01)
*A61B 17/11* (2006.01)

(52) U.S. Cl.
CPC .. *A61B 17/00491* (2013.01); *A61B 17/00234* (2013.01); *A61M 39/10* (2013.01); *A61B 17/1114* (2013.01); *A61B 2017/00296* (2013.01); *A61B 2017/00477* (2013.01); *A61B 2017/00946* (2013.01)

(58) Field of Classification Search
CPC .............. A61B 17/28; A61B 17/00234; A61B 17/00491; A61B 17/1114; A61B 2017/00477; A61B 2017/00296; A61B 2017/2905; A61B 17/08
See application file for complete search history.

(56) References Cited

U.S. PATENT DOCUMENTS

| 5,722,950 | A | 3/1998 | Fujita et al. |
|---|---|---|---|
| 5,989,215 | A | 11/1999 | Delmotte et al. |
| 6,228,051 | B1 | 5/2001 | Trumbull |
| 6,494,896 | B1 | 12/2002 | D'Alessio et al. |
| 6,540,716 | B1 | 4/2003 | Holm |
| 6,565,530 | B2 | 5/2003 | Sahatjian et al. |
| 6,689,148 | B2 | 2/2004 | Sawhney et al. |
| 6,695,815 | B2 | 2/2004 | Moenning |
| 6,835,186 | B1 | 12/2004 | Pennington et al. |
| 6,884,232 | B1 | 4/2005 | Hagmann et al. |
| 6,921,381 | B2 | 7/2005 | Spero et al. |
| 7,137,966 | B2 | 11/2006 | Sahatjian et al. |
| 7,601,147 | B2 | 10/2009 | Waller et al. |
| 7,766,868 | B2 | 8/2010 | Goode et al. |
| 7,955,315 | B2 * | 6/2011 | Feinberg .......... A61B 17/00491 604/528 |
| 7,963,944 | B2 | 6/2011 | Sahatjian et al. |
| 8,048,101 | B2 | 11/2011 | Lee-Sepsick et al. |
| 8,172,861 | B2 | 5/2012 | Fuller et al. |

(Continued)

OTHER PUBLICATIONS

International Search Report and Written Opinion in International Application No. PCT/US2015/066596, dated Apr. 1, 2016, 13 pages.

(Continued)

*Primary Examiner* — Victor Nguyen
(74) *Attorney, Agent, or Firm* — Fish & Richardson P.C.

(57) ABSTRACT

Devices for and methods that can be used in endoscopic surgery, and more particularly, devices and methods that can be used for endoscopically applying surgical sealants and other fluids to internal organs and tissues.

41 Claims, 6 Drawing Sheets

(56) References Cited

U.S. PATENT DOCUMENTS

| | | |
|---|---|---|
| 8,316,854 B2 | 11/2012 | Lee-Sepsick et al. |
| 8,336,552 B2 | 12/2012 | Lee-Sepsick et al. |
| 8,372,037 B2 | 2/2013 | Sahatjian et al. |
| 8,394,059 B2 | 3/2013 | Sahatjian et al. |
| 8,679,059 B2 | 3/2014 | Sahatjian et al. |
| 2004/0167473 A1 | 8/2004 | Moenning |
| 2007/0135826 A1* | 6/2007 | Zaver ............... A61B 17/0057 606/157 |
| 2009/0240109 A1 | 9/2009 | Ostrovsky et al. |
| 2014/0135825 A1 | 5/2014 | Tegels et al. |

OTHER PUBLICATIONS

International Preliminary Report on Patentability in International Application No. PCT/US2015/066596, dated Jun. 20, 2017, 8 pages.

\* cited by examiner

DEVICES FOR APPLYING SURGICAL SEALANTS

TECHNICAL FIELD

This document relates to devices that can be used in endoscopic or open surgery, and particularly to devices that can be used for applying surgical sealants or other fluids to organs and tissues.

BACKGROUND

Surgical sealants (e.g., the SYLYS® sealant available commercially from Cohera Medical, Inc.; Pittsburgh, Pa.) can be used to prevent leakage of fluids or gas post-surgery. There currently is no applicator available to efficiently and safely apply surgical sealants during endoscopic procedures or during open procedures in the body.

SUMMARY

This document is based at least in part on the development of a device designed for endoscopic (e.g., laparoscopic) application of surgical sealants. The device also can be an effective tool for application of various types of fluids that require endoscopic or open delivery in the body. This device can allow a user to maneuver into a body cavity during endoscopic or open surgery, articulate a delivery tube to a desired application angle, and readily apply an appropriate volume of sealant (or any suitable fluid) to the surface of a desired area. For example, the device can be used to reach into the lower pelvis of a patient and apply a sealant during bowel anastomosis procedures, including open bowel anastomosis procedures and endoscopic procedures.

In one aspect, this document features an endoscopic device having: an elongate outer tube having a first end, a second end, and a lumen extending axially between the first and second ends of the outer tube, wherein the outer tube comprises a rigid material; an elongate inner tube having a first end, a second end, and one or more lumens and a wire core that extend axially between the first and second ends of the inner tube, wherein the inner tube comprises a flexible material, and wherein the inner tube is positioned within the outer tube; a hub configured to receive and retain the first end of the outer tube and the first end of the inner tube; and a connector fitting configured to engage the hub and a vessel.

The outer tube can contain stainless steel. In some embodiments, the outer tube can have a length between about 33 cm and about 43 cm, and an external diameter between about 4 mm and about 6 mm.

The inner tube can have four lumens extending axially between the first and second ends of the inner tube, and/or a polyether block amide formulation. In some embodiments, the inner tube can have a length between about 35 cm and about 45 cm, and an external diameter between about 2 mm and about 4 mm. The wire core can contain stainless steel. In some embodiments, the wire core can have a diameter between about 0.5 mm and about 2 mm.

The inner tube can be positioned within the lumen of the outer tube such that the first end of the inner tube extends beyond the first end of the outer tube, and the second end of the inner tube extends beyond the second end of the outer tube.

The hub can have a first end, a second end, a lumen extending axially between the first and second ends of the hub, and an interior surface that defines a protrusion, wherein the protrusion defines the boundaries of a first cavity and a second cavity. The first cavity can be configured to receive and engage a connector fitting, and the second cavity can be configured to receive and retain the first end of the outer tube. The first end of the outer tube can be secured within the second cavity of the hub by a laser weld. The interior surface of the first cavity can define threading configured to receive threading on the connector fitting, such that the connector fitting can be engaged within the first cavity. The connector fitting can be secured within the first cavity by an adhesive. In some embodiments, the connector fitting can be a female connector fitting.

The device can further have a collar positioned within the second cavity of the hub, wherein the collar is configured to engage the first end of the inner tube. The first end of the inner tube can be attached to the collar by an adhesive.

In another aspect, this document features a method for applying a surgical fluid to a tissue in a patient. The method can include (a) providing an endoscopic device having (i) an elongate outer tube having a proximal end, a distal end, and a lumen extending axially between the proximal and distal ends of the outer tube, wherein the outer tube comprises a rigid material; (ii) an elongate inner tube having a proximal end, a distal end, and one or more lumens and a wire core that extend axially between the proximal and distal ends of the inner tube, wherein the inner tube comprises a flexible material, and wherein the inner tube is positioned within the outer tube such that the distal end of the inner tube extends from the distal end of the outer tube; (iii) a hub configured to receive and retain the proximal end of the outer tube and the proximal end of the inner tube; and (iv) a connector fitting engaged with the hub and a vessel containing the surgical fluid; (b) inserting a portion of the endoscopic device into the patient such that the distal tip of the inner tube is positioned adjacent to the tissue to which the surgical fluid is to be applied; (c) manipulating the distal end of the inner tube, to direct the distal end toward the portion of the tissue to which the surgical fluid is to be applied; and (d) actuating the vessel such that the surgical fluid passes through the one or more lumens of the inner tube and contacts the tissue.

The outer tube can contain stainless steel. The inner tube can have four lumens extending axially between the proximal and distal ends of the inner tube. The inner tube can have a polyether block amide formulation. The wire core can contain stainless steel. The vessel can be a syringe. The method can include inserting a portion of the endoscopic device into the patient through an opening in the body (e.g., through a trocar). The method can include manipulating the distal end of the inner tube with a grasping device inserted into the patient.

The surgical fluid can be a sealant. The patient can be undergoing closure of an anastomotic junction in the gastrointestinal tract, a bowel anastomosis procedure, or an arthroscopic procedure.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document provides devices and methods for targeted delivery of surgical sealants (or other fluids) within the body during endoscopic or open surgeries. The devices provided herein can allow a user to maneuver into a body cavity during a surgical procedure, articulate a delivery tube to a desired application angle, and apply an appropriate volume of fluid to a desired area. For example, the devices disclosed herein can be used to reach into the lower pelvis of a patient and apply a sealant during a bowel anastomosis procedure.

In general, the devices provided herein include an elongate outer tube and an elongate inner tube, where the inner tube has a co-extruded wire core and two or more lumens extending between its first and second ends. The outer tube can be rigid, while the inner tube can be flexible. The inner tube fits within the outer tube, and a first end (e.g., the proximal end) of each tube is held within a single hub. The second end (e.g., the distal end) of the inner tube extends beyond the second end of the outer tube, and due to the presence of the co-extruded wire core, can be bent by a user to a desired angle. The hub also has a means for connecting to a vessel (e.g., a syringe) containing a fluid to be delivered through the device.

Figure 1A:
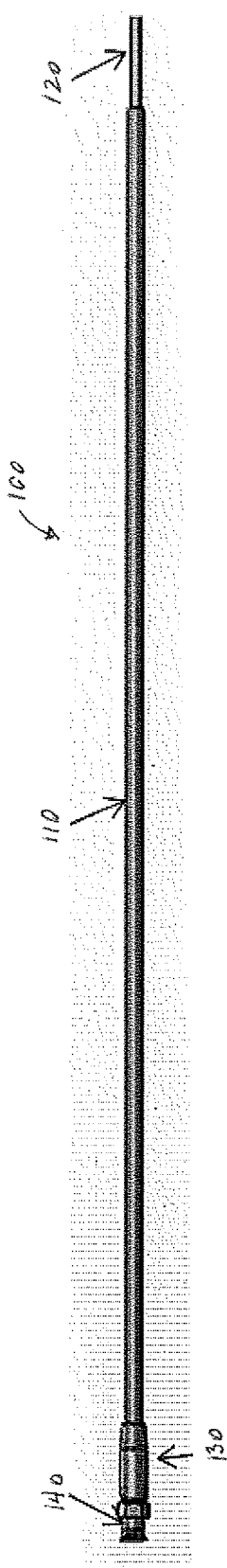
FIG. 1A is a side view of an embodiment of an endoscopic applicator device as provided herein.
Figure 1B:
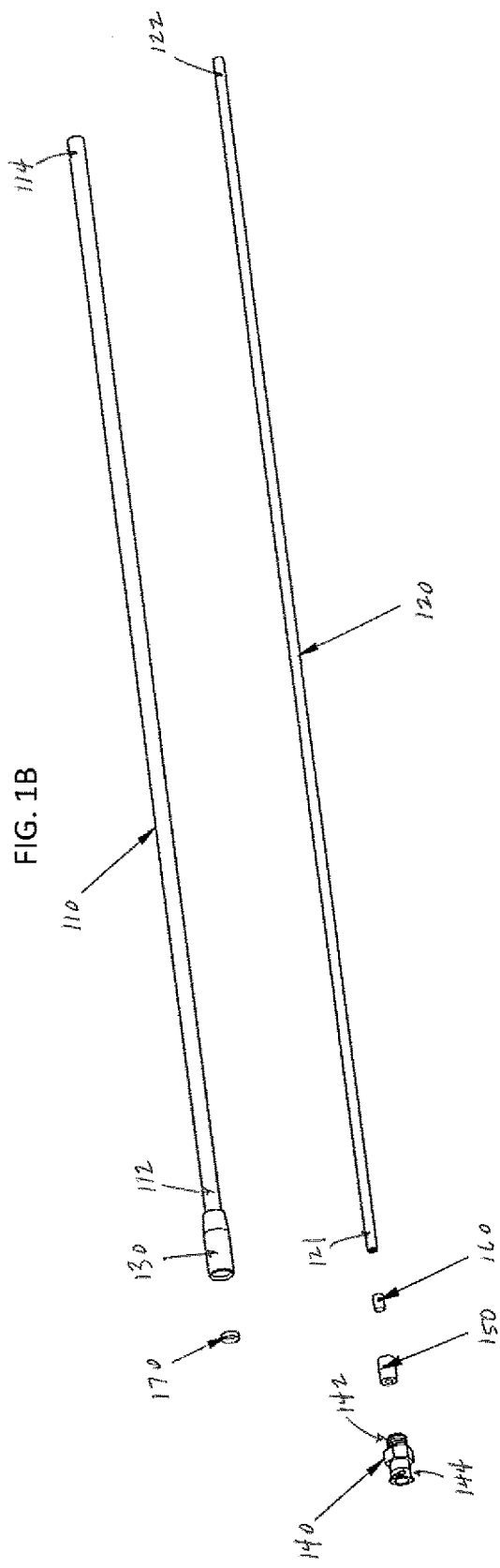
FIG. 1B is an exploded view of the embodiment shown in FIG. 1A.

An exemplary embodiment of such a device is depicted in FIGS. 1A and 1B. The device 100 can have an outer tube 110, an inner tube 120, and a hub 130. In addition, the device 100 can include a connector fitting 140 that can be connected to the hub 130, and a collar 150 that can fit within the hub 130 for attachment of the inner tube 120, as described below. In some embodiments, the connector fitting 140 can be a luer fitting. As depicted in FIG. 1B, the device 100 also can include a first adhesive 160 and a second adhesive 170, which can attach various elements of the device 100 to one another.

Figure 2A:
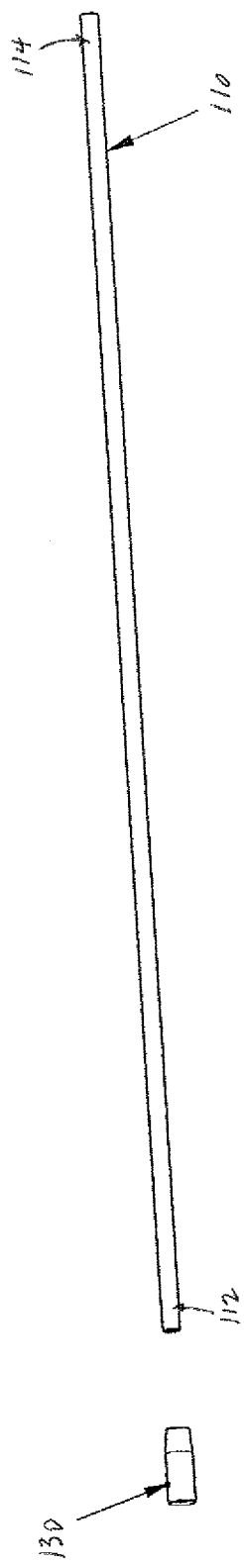
FIG. 2A is an exploded view of an outer tube and a hub from an embodiment of an endoscopic device as provided herein.
Figure 2B:
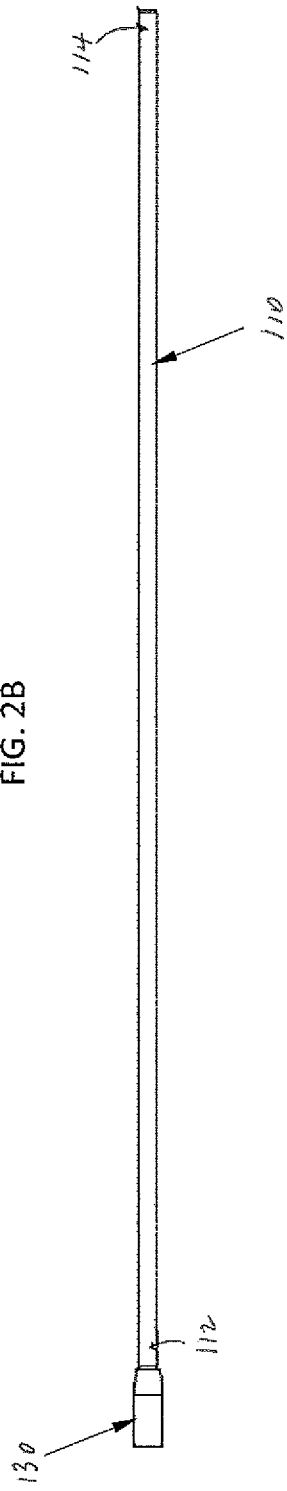
FIG. 2B is a side view of the outer tube of FIG. 2A assembled with the hub.

With further reference to FIGS. 1A and 1B, and also to FIGS. 2A and 2B, the device 100 can have an outer shell that includes the outer tube 110 and the hub 130. The outer tube 110 can have a proximal end 112, a distal end 114, and a lumen extending axially through the outer tube 110 between the proximal and distal ends 112 and 114. The proximal end 112 of the outer tube 110 can be configured to fit snugly into the hub 130. The outer tube 110 can be made from a rigid material (e.g., stainless steel, extrudable plastics such as polypropylene or polyethylene, or other commonly used, surgically safe machinable metals), which can provide sufficient structural support to allow a user to readily maneuver the distal end 114 to the intended application area. The outer tube 110 can have a length between about 7 cm and about 67 cm. In some embodiments, for example, the outer tube 110 can have a length between about 7 and about 27 cm (e.g., for open procedures), between about 30 and about 40 cm (e.g., for general procedures), or between about 57 and about 67 cm (e.g., for bariatric procedures). In some embodiments, the outer tube 110 can have a length between about 33 and about 43 cm. In addition, the outer tube 110 can be configured to fit through a trocar or surgical opening. Thus, the exterior diameter of the outer tube 110 can be limited by the dimensions of the trocar or opening created for the procedure. In some embodiments, for example, the outer tube 110 can have an external diameter between about 4 mm and about 10 mm (e.g., between about 4 and about 6 mm, between about 5 and about 7 mm, between about 6 and about 8 mm, between about 7 and about 9 mm, or between about 8 and about 10 mm). In some embodiments, the exterior diameter of the outer tube 110 can be between about 4 and about 5 mm. Further, the lumen of the outer tube 110 can have a diameter between about 2 mm and about 9 mm (e.g., between about 2 and about 4 mm, between about 3 and about 6 mm, or between about 5 and about 7 mm). In some embodiments, for example, the lumen of the outer tube 110 can have a diameter between about 3 and about 4 mm. Typically, the lumen of the outer tube 110 can have a diameter that is coincident or slightly greater than the outer diameter of the inner tube 120.

Figure 3A:
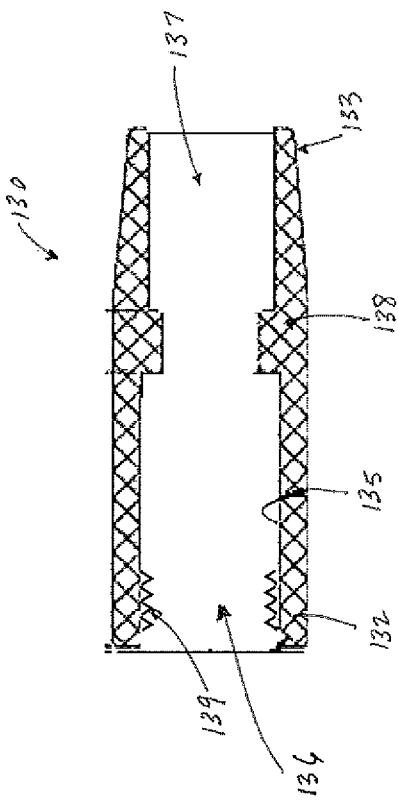
FIG. 3A is a cross-sectional view of an embodiment of a hub as provided herein.
Figure 3B:
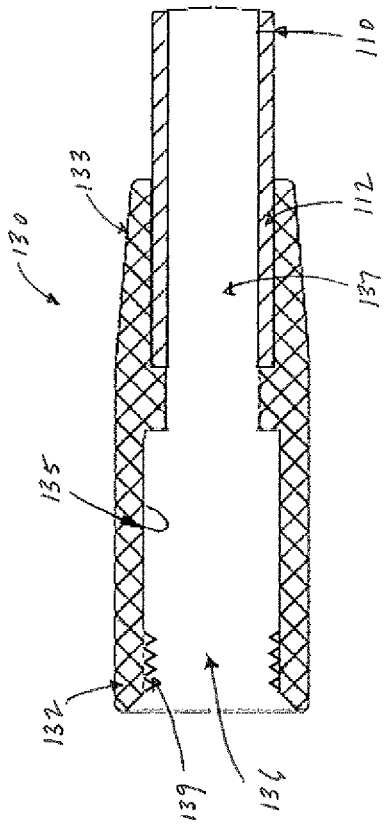
FIG. 3B is a cross-sectional view of the hub of FIG. 3A, engaged with an end of an outer tube.

Referring now to FIGS. 3A and 3B, the hub 130 can have a proximal end 132, a distal end 133, and an interior surface 135 defining a lumen that extends axially between the proximal and distal ends 132 and 133. The interior surface 135 can define a proximal cavity 136, a distal cavity 137, and a circumferential protrusion 138 that can define the boundaries of the proximal and distal cavities 136 and 137. The distal cavity 137 can be configured to receive the proximal end 112 of the outer tube 110, which can be secured within the distal cavity 137 using a suitable means (e.g., a laser weld or a press fit, or with an adhesive such as an epoxy). The hub can be made from, for example, stainless steel, machinable plastics such as polypropylene or polyethylene, or surgically safe, machinable metal. The length of the hub 130 between the proximal end 132 and the distal end 133 can be sufficient to effectively secure the outer tube 110 to the distal end 133 and create an interface at the proximal end 132 for the attachment of the connector fitting 140. For example, in some embodiments, the hub 103 can have a length between about 1 cm and about 6 cm. In some embodiments, the length of the hub 130 can be between about 1 and about 3 cm, between about 2 and about 4 cm, or between about 4 and about 6 cm. In some cases, the hub 130 can have a length between about 1 and about 2 cm, or between about 2 and about 3 cm. Since the distal cavity 137 can be configured to receive the proximal end 112 of the outer tube 110, diameter of the distal cavity 137 can be dependent on the external diameter of the outer tube 110, such that it is slightly greater than the external diameter of the outer tube 110. In some embodiments, the diameter of the distal cavity 137 can be between about 5 mm and about 14 mm (e.g., between about 5 and about 8 mm, between about 6 and about 9 mm, between about 7 and about 10 mm, between about 8 and about 11 mm, between about 9 and about 12 mm, between about 10 and about 13 mm, or between about 11 and about 14 mm).

The interior surface 135 of the proximal cavity 136 can be tapped to define threading 139. The threading 139 within the hub 130 can provide a junction for the connector fitting 140. The connector fitting 140 can have, for example, threading 142 (e.g., 1/4-28 UNF threading) to mate with the threading 139 within the hub 130, and a female fitting 144 to mate with a vessel containing a material to be applied. The connector fitting 140 can be attached to the hub 130 using, for example, the threading, first adhesive 160 (e.g., medical grade cyanoacrylate, epoxy, or another suitable adhesive), or any other appropriate type of interface. The female connector fitting 144 can allow any vessel (e.g., a syringe) to be attached to the device 100.

Figure 4C:
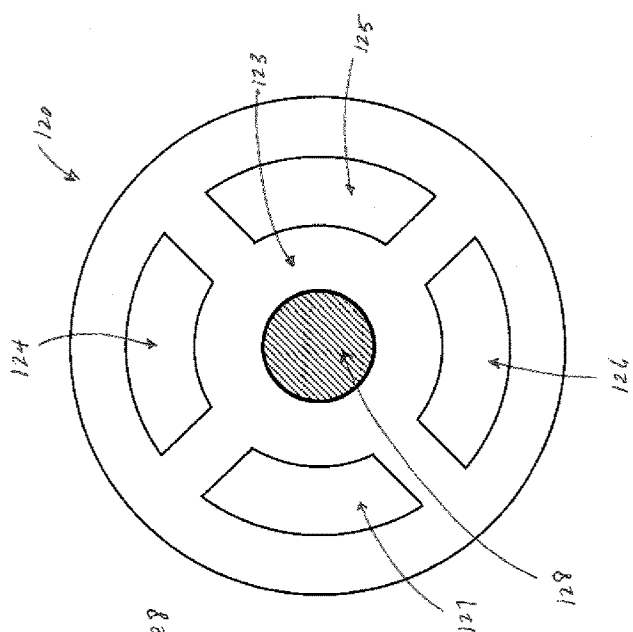
FIG. 4C is a cross-sectional view of an embodiment of an inner tube that can be included in an endoscopic device as provided herein, where the inner tube has four lumens.
Figure 4B:
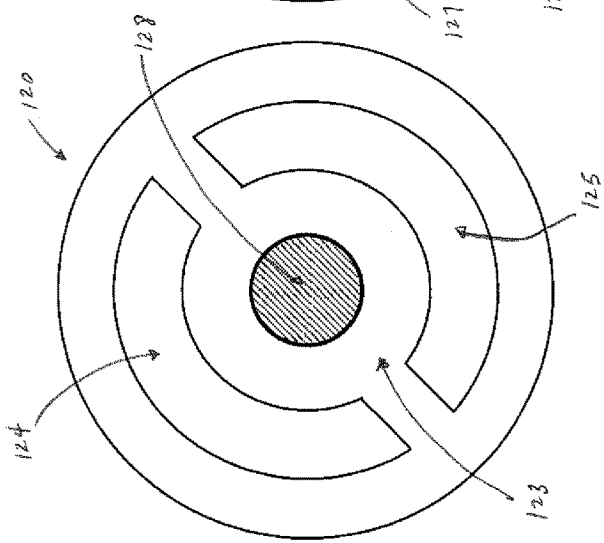
FIG. 4B is a cross-sectional view of an embodiment of an inner tube that can be included in an endoscopic device as provided herein, where the inner tube has two lumens.
Figure 4A:
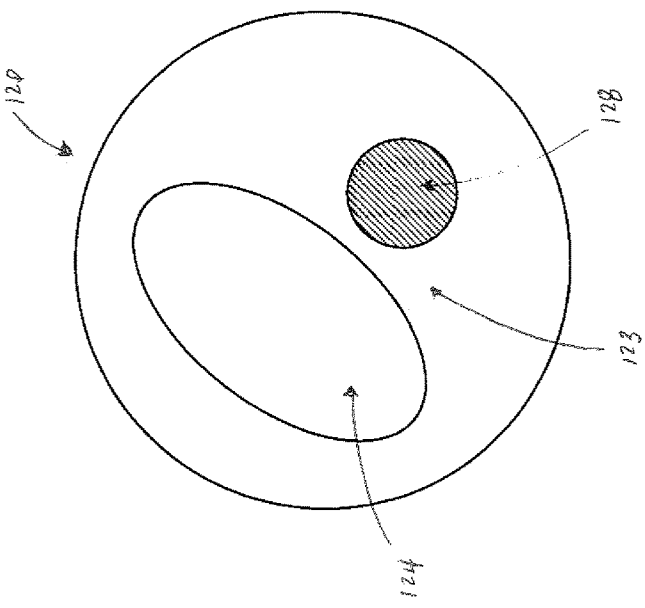
FIG. 4A is a cross-sectional view of an embodiment of an inner tube that can be included in an endoscopic device as provided herein, where the inner tube has one lumen.

Within the outer tube 110 is the inner tube 120, embodiments of which are shown in the cross-sectional views of FIGS. 4A-4C. The inner tube 120 can have a proximal end 121 and a distal end 122 (shown in FIG. 1B, for example), and can have one, two, three, four, or more than four lumens extending axially between the proximal and distal ends 121 and 122. As shown in FIGS. 4A-4C, for example, the inner tube 120 can have a core 123 and a lumen 124 (FIG. 4A), or a core 123 and lumens 124 and 125 arranged around the core 123 (FIG. 4B), or a core 123 and lumens 124, 125, 126, and 127 arranged around the core 123 (FIG. 4C). The presence of more than one lumen can allow a fluid (e.g., a viscous surgical fluid such as a sealant) to flow through the device 100 in a restricted manner, thus limiting the amount of fluid applied. Restriction of flow can be dependent on the cross sectional area of the lumens, for example. The multiple lumens also can facilitate uniform application of the fluid over a desired area, and can minimize clogging by preventing sealant from curing within the lumens. If one lumen becomes clogged, pinched, or occluded, the fluid can flow through the remaining lumens.

The length of the inner tube 120 can be dependent on the length of the outer tube 110. For example, the inner tube 120 can have a length between about 18 cm and about 68 cm. In some embodiments, the inner tube 120 can have a length between about 18 and about 28 cm, between about 28 and about 38 cm, between about 38 and about 48 cm, between about 48 and about 58 cm, or between about 58 and about 68 cm. In some embodiments, the inner tube 120 can have a length between about 35 and about 45 cm.

In addition, the inner tube 120 can be configured to fit through the lumen of the outer tube 110. Thus, the external diameter of the inner tube 120 can be coincident or slightly smaller than the inner diameter of the outer tube 110. In some embodiments, the inner tube 120 can have an external diameter between about 2 mm and about 7 mm (e.g., between about 2 and about 4 mm, between about 3 and about 5 mm, between about 4 and about 6 mm, or between about 5 and about 7 mm). In some embodiments, for example, the inner tube 120 can have an exterior diameter between about 2 and about 3 mm, or between about 3 and about 4 mm. In general, the inner tube 120 can have a length that is slightly longer than that of the outer tube 110, such that when the inner tube 120 is placed within the lumen of the outer tube 110, the proximal end 121 of the inner tube 120 extends beyond the proximal end 112 of the outer tube 110, and the distal end 122 of the inner tube 120 extends beyond the distal end 114 of the outer tube 110. For example, when the proximal end 121 of the inner tube 120 and the proximal end 122 of the distal end 122 are positioned within the proximal and distal cavities 136 and 137 of the hub 130, the inner tube 120 can extend about 0.5 cm to about 5 cm (e.g., between about 0.5 and about 2 cm, between about 1 and about 3 cm, between about 2 and about 4 cm, or between about 3 and about 5 cm) beyond the distal end 114 of the outer tube 110. It is to be noted that the overall length of the distal end 122 of the inner tube 120 extending beyond the distal end 114 of the outer tube 110 can be adjusted based on the procedure.

The inner tube 120 generally is flexible, and can be made from any of a variety of suitable materials, including polyether block amide formulations, soft polyurethanes (e.g., PELLETHANE® 2363-80AE; Lubrizol Advanced Materials, Inc., Cleveland, Ohio), and soft polyvinylchloride (PVC) materials. In some embodiments, for example, the inner tube 120 can be made of the polyether block amide PEBAX® 3533 SA01 MED (Arkema Specialty Polyamides, France).

Figure 5A:
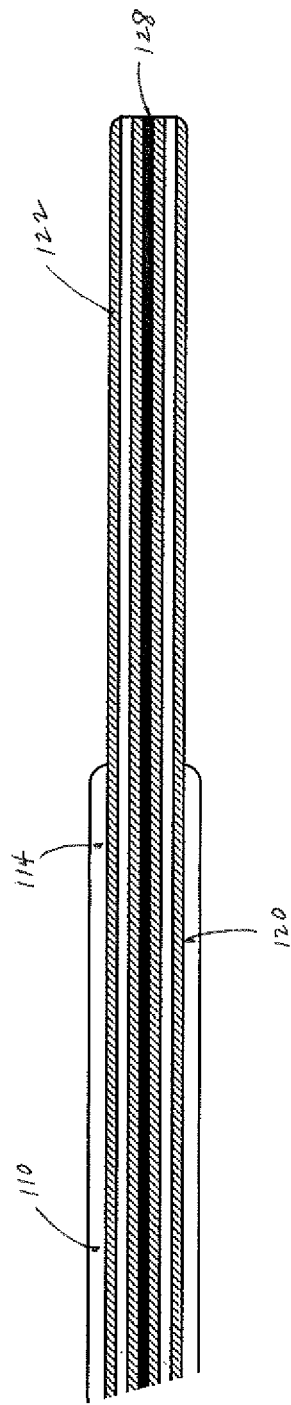
FIG. 5A is a cross-sectional view of an embodiment of the distal end of a device as provided herein, showing an inner tube protruding from the distal end of an outer tube.
Figure 5B:
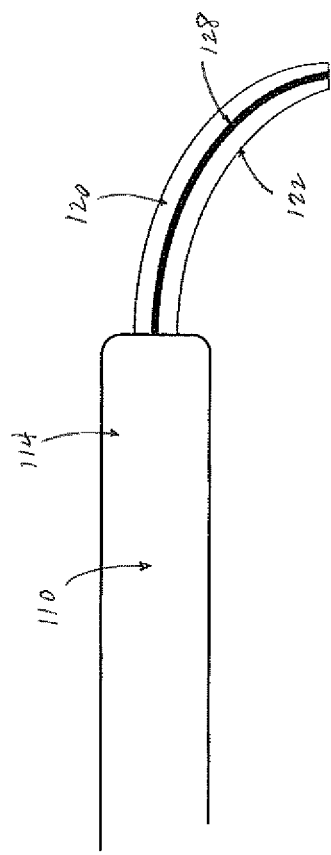
FIG. 5B is a side view of a distal end as shown in FIG. 5A, where the distal end is in a bent configuration.

The core 123 of the inner tube 120 can contain a co-extruded wire 128, which can allow a user to bend the distal end 122 of the inner tube 120 into a desired position. As depicted in FIGS. 5A and 5B, for example, the distal end 122 of the inner tube 120 can extend beyond the distal end 114 of the outer tube 110, and the wire 128 can be bent by a user to direct the distal end 122 to a desired target within a body. The central position of the co-extruded wire 128 in the core 123 of the inner tube 120 can allow for equal bending of the distal end 122 in any direction. The co-extruded wire can be made from stainless steel, or from any other thin gage, surgically safe metal. The diameter of the wire 128 can be determined at least in part by the outer diameter of the inner tube 120. For example, the wire 128 can have a diameter of about 0.5 mm to about 2 mm (e.g., between about 0.5 and about 1 mm, between about 1 and about 1.5 mm, or between about 1.5 and about 2 mm). The wire 128 can have a length that is essentially the same as the length of the inner tube 120 (e.g., between about 7 cm and about 67 cm). It is to be noted that the end of the wire 128 at the distal end 122 of the inner tube 120 can be trimmed back by about 0.3 to about 2 mm (e.g., about 0.3, 0.5, 0.7, 0.9, 1, 1.3, 1.6, or 2 mm) so that the wire 138 does not come into contact with bodily tissues or organs during use, thus reducing the risk of damage to tissue during application of a surgical fluid within a patient, for example.

Figure 6A:
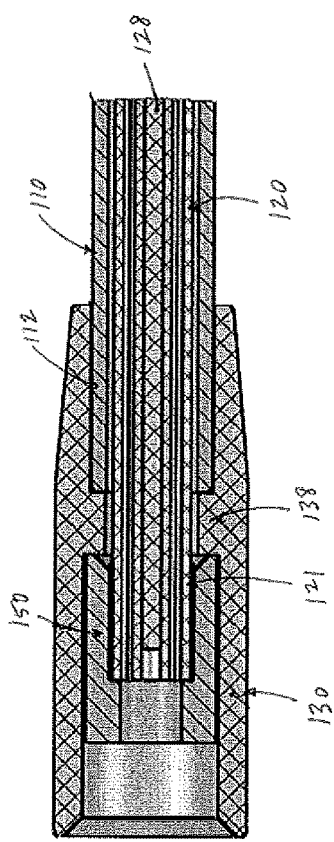
FIG. 6A is a cross-sectional view of an embodiment of the proximal end of a device as provided herein, showing a hub engaged with an outer tube, a collar, and an inner tube.
Figure 6B:
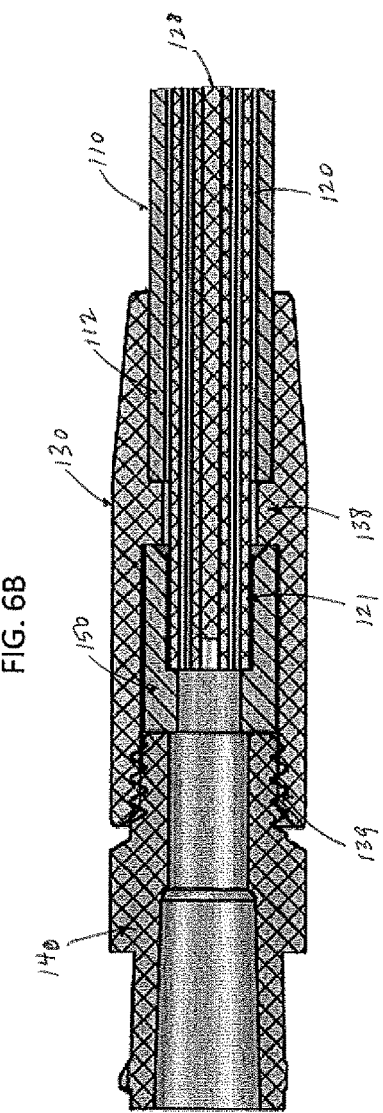
FIG. 6B is a cross-sectional view of a proximal end as shown in FIG. 6A, with the hub being further engaged with a connector fitting.

As shown in FIGS. 6A and 6B, the proximal end 121 of the inner tube 120 can be secured within the hub 130 by the collar 150. In some embodiments, the collar can be a one-sided part, which can facilitate assembly of the device 100, and can create a seal within the hub 130. The proximal end 121 of the inner tube 120 can be affixed to the collar 150 using the second adhesive 170 (e.g., a UV curable adhesive, epoxy, or cyanoacrylate).

In some embodiments, during manufacturing and assembly of the device 100, the hub 130 can be attached (e.g., welded) to the proximal end 112 of the outer tube 110, the collar 150 can be adhered to the inner tube 120 (e.g., using an adhesive), and the distal end 122 of the inner tube 120 can then be passed through the hub 130 and the outer tube 110, until the collar 150 comes into contact with the circumferential protrusion 138 of the hub 130. The connector fitting 140 then can be installed via the threading 139 and the first adhesive, for example.

In use, the distal tip 122 of the inner tube 120 can be manipulated manually or mechanically (e.g., using a grasper device inserted into the surgical field), until the distal tip 122 achieves a desired configuration. The distal tip 122 can retain its shape until it is again manipulated by a user. A vessel (e.g., a syringe) containing a sealant or other surgical fluid can be attached to the connector fitting 140, and the vessel can be actuated to pass a sealant or other fluid through the device 100. In addition to being useful with open bowel anastomosis procedures, the devices provided herein may be useful for endoscopic approaches to other sites in the gastrointestinal tract, such as the stomach (e.g., for obesity surgeries) or the esophagus, for example. Thus, in some embodiments, the devices and methods provided herein can be useful as an adjunct to closure of anastomotic junctions in the gastrointestinal tract. In some embodiments, the devices and methods provided herein also can be useful in arthroscopic procedures.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. An endoscopic device comprising:
an elongate outer tube having a first end, a second end, and a lumen extending axially between the first and second ends of the outer tube, wherein the outer tube comprises a rigid material;
an elongate inner tube having a first end, a second end, and one or more lumens and a wire core that extend axially between the first and second ends of the inner tube, wherein the inner tube comprises a flexible material, and wherein the inner tube is positioned within the outer tube;
a hub that receives and retains the first end of the outer tube and the first end of the inner tube, wherein the hub comprises a first end, a second end, a lumen extending axially between the first and second ends of the hub, and an interior surface that defines a protrusion, wherein the protrusion defines the boundaries of a first cavity and a second cavity within the hub; and
a connector fitting engaged with the hub and configured to engage a vessel.
2. The device of claim 1, wherein the outer tube comprises stainless steel.

3. The device of claim 1, wherein the outer tube has a length between about 33 cm and about 43 cm, and an external diameter between about 4 mm and about 6 mm.
4. The device of claim 1, wherein the inner tube has four lumens extending axially between the first and second ends of the inner tube.
5. The device of claim 1, wherein the inner tube comprises a polyether block amide formulation.
6. The device of claim 1, wherein the inner tube has a length between about 35 cm and about 45 cm, and an external diameter between about 2 mm and about 4 mm.
7. The device of claim 1, wherein the wire core comprises stainless steel.
8. The device of claim 1, wherein the wire core has a diameter between about 0.5 mm and about 2 mm.
9. The device of claim 1, wherein the inner tube is positioned within the lumen of the outer tube such that the first end of the inner tube extends beyond the first end of the outer tube, and the second end of the inner tube extends beyond the second end of the outer tube.
10. The device of claim 1, wherein the first cavity is configured to receive and engage a connector fitting, and wherein the second cavity is configured to receive and retain the first end of the outer tube.
11. The device of claim 10, wherein the first end of the outer tube is secured within the second cavity of the hub by a laser weld.
12. The device of claim 10, wherein the interior surface of the first cavity defines threading configured to receive threading on the connector fitting, such that the connector fitting is engaged within the first cavity.
13. The device of claim 10, wherein the connector fitting is secured within the first cavity by an adhesive.
14. The device of claim 10, wherein the connector fitting is a female connector fitting.
15. The device of claim 1, further comprising a collar positioned within the second cavity of the hub, wherein the collar is configured to engage the first end of the inner tube.
16. The device of claim 15, wherein the first end of the inner tube is attached to the collar by an adhesive.
17. A method for applying a surgical fluid to a tissue in a patient, comprising:
(a) providing an endoscopic device comprising:
(i) an elongate outer tube having a proximal end, a distal end, and a lumen extending axially between the proximal and distal ends of the outer tube, wherein the outer tube comprises a rigid material;
(ii) an elongate inner tube having a proximal end, a distal end, and one or more lumens and a wire core that extend axially between the proximal and distal ends of the inner tube, wherein the inner tube comprises a flexible material, and wherein the inner tube is positioned within the outer tube such that the distal end of the inner tube extends from the distal end of the outer tube;
(iii) a hub that receives and retains the proximal end of the outer tube and the proximal end of the inner tube, wherein the hub comprises a first end, a second end, a lumen extending axially between the first and second ends of the hub, and an interior surface that defines a protrusion, wherein the protrusion defines the boundaries of a first cavity and a second cavity; and
(iv) a connector fitting engaged with the hub and a vessel containing the surgical fluid;

(b) inserting a portion of the endoscopic device into the patient such that the distal tip of the inner tube is positioned adjacent to the tissue to which the surgical fluid is to be applied;

(c) manipulating the distal end of the inner tube, to direct the distal end toward the portion of the tissue to which the surgical fluid is to be applied; and (d) actuating the vessel such that the surgical fluid passes through the one or more lumens of the inner tube and contacts the tissue.

18. The method of claim 17, wherein the outer tube comprises stainless steel.

19. The method of claim 17, wherein the inner tube has four lumens extending axially between the proximal and distal ends of the inner tube.

20. The method of claim 17, wherein the inner tube comprises a polyether block amide formulation.

21. The method of claim 17, wherein the wire core comprises stainless steel.

22. The method of claim 17, wherein the vessel is a syringe.

23. The method of claim 17, comprising inserting a portion of the endoscopic device into the patient through an opening in the body.

24. The method of claim 17, comprising inserting a portion of the endoscopic device into the patient through a trocar.

25. The method of claim 17, comprising manipulating the distal end of the inner tube with a grasping device inserted into the patient.

26. The method of claim 17, wherein the surgical fluid is a sealant.

27. The method of claim 17, wherein the patient is undergoing closure of an anastomotic junction in the gastrointestinal tract.

28. The method of claim 17, wherein the patient is undergoing a bowel anastomosis procedure.

29. The method of claim 17, wherein the patient is undergoing an arthroscopic procedure.

30. An endoscopic device comprising:

an elongate outer tube having a first end, a second end, and a lumen extending axially between the first and second ends of the outer tube, wherein the outer tube comprises a rigid material;

an elongate inner tube having a first end, a second end, and one or more lumens and a wire core that extend axially between the first and second ends of the inner tube, wherein the inner tube comprises a flexible material, and wherein the inner tube is positioned within the outer tube;

a hub that receives and retains the first end of the outer tube and the first end of the inner tube, wherein the hub comprises a first end, a second end, a lumen extending axially between the first and second ends of the hub, and an interior surface that defines a protrusion, wherein the protrusion defines the boundaries of a first cavity and a second cavity, wherein the first cavity is configured to receive and engage a connector fitting, and wherein the second cavity is configured to receive and retain the first end of the outer tube, and wherein the interior surface of the first cavity defines threading configured to receive threading on the connector fitting, such that the connector fitting is engaged within the first cavity; and the connector fitting engaged with the hub and configured to engage a vessel.

31. The device of claim 30, wherein the outer tube comprises stainless steel.

32. The device of claim 30, wherein the outer tube has a length between about 33 cm and about 43 cm, and an external diameter between about 4 mm and about 6 mm.

33. The device of claim 30, wherein the inner tube has four lumens extending axially between the first and second ends of the inner tube.

34. The device of claim 30, wherein the inner tube comprises a polyether block amide formulation.

35. The device of claim 30, wherein the inner tube has a length between about 35 cm and about 45 cm, and an external diameter between about 2 mm and about 4 mm.

36. The device of claim 30, wherein the wire core comprises stainless steel.

37. The device of claim 30, wherein the wire core has a diameter between about 0.5 mm and about 2 mm.

38. The device of claim 30, wherein the inner tube is positioned within the lumen of the outer tube such that the first end of the inner tube extends beyond the first end of the outer tube, and the second end of the inner tube extends beyond the second end of the outer tube.

39. The device of claim 30, wherein the first end of the outer tube is secured within the second cavity of the hub by a laser weld.

40. The device of claim 30, further comprising a collar positioned within the second cavity of the hub, wherein the collar is configured to engage the first end of the inner tube.

41. The device of claim 40, wherein the first end of the inner tube is attached to the collar by an adhesive.

\* \* \* \* \*